United States Patent
Parsley et al.

(10) Patent No.: US 9,676,641 B2
(45) Date of Patent: Jun. 13, 2017

(54) THERAPEUTIC PHAGES AND METHODS FOR DELIVERY OF NUCLEIC ACIDS FOR THERAPEUTIC USES

(71) Applicant: SynPhaGen LLC., Gaithersburg, MD (US)

(72) Inventors: Todd Bernard Parsley, Montgomery Village, MD (US); Christian Furlan Freguia, Germantown, MD (US)

(73) Assignee: SynPhaGen LLC, North Potomac, MD (US)

( * ) Notice: Subject to any disclaimer, the term of this patent is extended or adjusted under 35 U.S.C. 154(b) by 0 days.

(21) Appl. No.: 14/605,320

(22) Filed: Jan. 26, 2015

(65) Prior Publication Data

US 2016/0160186 A1    Jun. 9, 2016

Related U.S. Application Data

(60) Provisional application No. 62/088,073, filed on Dec. 5, 2014, provisional application No. 62/063,031, filed on Oct. 13, 2014, provisional application No. 61/933,032, filed on Jan. 29, 2014.

(51) Int. Cl.
| | |
|---|---|
| *A61K 35/76* | (2015.01) |
| *C12N 7/01* | (2006.01) |
| *C12N 7/04* | (2006.01) |
| *C12N 15/63* | (2006.01) |
| *C02F 3/34* | (2006.01) |
| *C12N 15/86* | (2006.01) |
| *C12N 15/113* | (2010.01) |
| *C12N 15/11* | (2006.01) |

(52) U.S. Cl.
CPC ........... *C02F 3/34* (2013.01); *C12N 15/86* (2013.01); *C12N 15/111* (2013.01); *C12N 15/113* (2013.01); *C12N 2310/14* (2013.01); *C12N 2320/32* (2013.01); *C12N 2330/50* (2013.01); *C12N 2795/14143* (2013.01); *C12N 2820/55* (2013.01)

(58) Field of Classification Search
None
See application file for complete search history.

(56) References Cited

U.S. PATENT DOCUMENTS

| | | | |
|---|---|---|---|
| 6,271,034 B1 * | 8/2001 | Bardarov et al. | 435/472 |
| 8,227,242 B2 | 7/2012 | Bradbury | |
| 2001/0014463 A1 | 8/2001 | Delisle | |
| 2003/0104604 A1 | 6/2003 | Yang | |
| 2003/0148501 A1 | 8/2003 | Picardal | |
| 2005/0107326 A1 | 5/2005 | Norris | |
| 2007/0128728 A1 | 6/2007 | Bradbury | |
| 2008/0305119 A1 | 12/2008 | Dewhurst et al. | |
| 2009/0148408 A1 | 6/2009 | Chang | |
| 2010/0047885 A1 | 2/2010 | Lee | |
| 2010/0226890 A1 | 9/2010 | Holland | |
| 2010/0239546 A1 | 9/2010 | Fruehauf | |
| 2010/0240025 A1 | 9/2010 | Read | |
| 2012/0070414 A1 | 3/2012 | Stamets | |
| 2013/0011898 A1 | 1/2013 | Szpirer | |

FOREIGN PATENT DOCUMENTS

| | | |
|---|---|---|
| WO | WO 9805344 | 2/1998 |
| WO | WO 03076583 | 9/2003 |
| WO | WO 2005046579 | 6/2004 |
| WO | WO 2014160418 | 10/2014 |

OTHER PUBLICATIONS

Hagens et al., Therapy of Experimental Pseudomonas Infections with a Nonreplicating Genetically Modified Phage. Antimicrobial Agents and Chemotherapy, 2004, vol. 48, p. 3817-3822.*
Ferreira et al., Bacillus subtilis as a tool for vaccine development: from antigen factories to delivery vectors. Annals of the Brazilian Academy of Sciences. (2005) 77(1): 113-124.*
Agilent Technologies, pBC Phagemids Instruction Manual. Revision A.01, 2008, pp. 1-27.*

* cited by examiner

*Primary Examiner* — Kevin Hill
*Assistant Examiner* — Arthur S Leonard

(57) ABSTRACT

Compositions for a phage particle are disclosed. The phage particle is non-replicating and includes at least one heterologous nucleic acid sequence that is capable of being expressed in a target bacteria. The expressed heterologous nucleic acid sequence is non-lethal to the target bacteria.

13 Claims, 3 Drawing Sheets

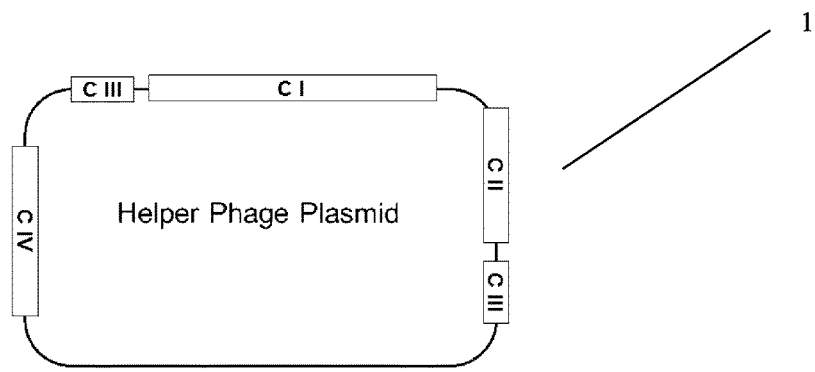

- Cassette I (C I): DNA encoding helper phage proteins necessary for replication and packaging of heterologous sequences.
- Cassette II (C II): Metabolic marker for non-antibiotic selection in transformed bacterial host strain.
- Cassette III (C III): DNA sequences necessary for integration into the bacterial host genome.
- Cassette IV (C IV): DNA elements necessary for cloning and amplification of helper phage plasmid used for bacterial transformation.

Fig. 1

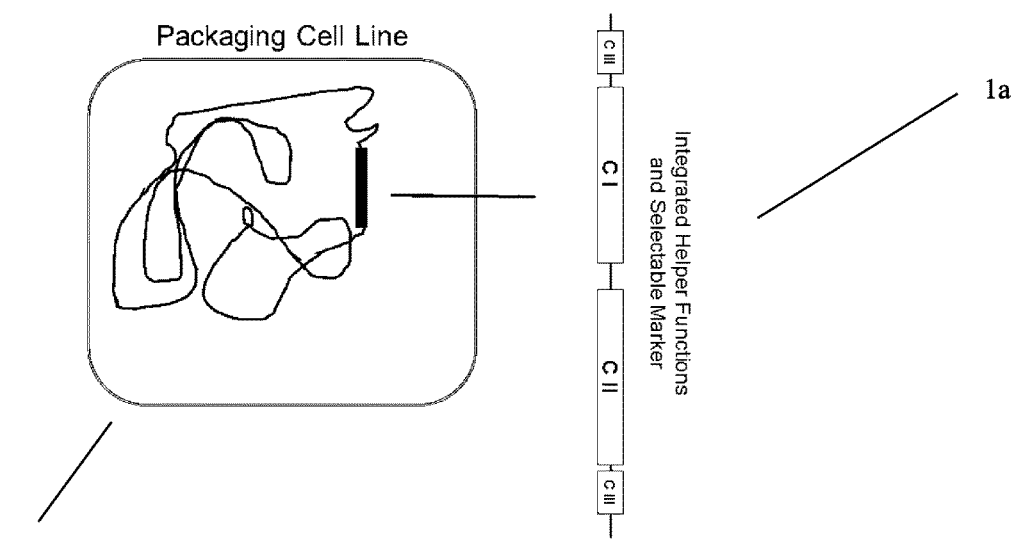

Fig. 2

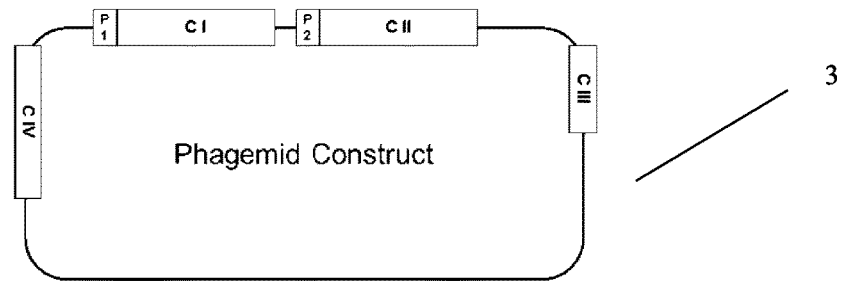

- Cassette I (C I): DNA encoding phage proteins necessary for synthesis and packaging of the phage genome into the infectious particle and maintenance in the infected bacteria.
- Cassette II (C II): DNA sequences encoding the therapeutic gene(s).
- Cassette III (CIII): DNA module encoding bacterial receptor binding protein.
- Cassette IV (C IV): DNA elements necessary for cloning and amplification of helper phage plasmid used for bacterial transformation.
- Promoter I (P1) – Promoter for expression of phage genes.
- Promoter II (P2) – Bacterial promoter for expression of therapeutic genes.

Fig. 3

THERAPEUTIC PHAGES AND METHODS FOR DELIVERY OF NUCLEIC ACIDS FOR THERAPEUTIC USES

CLAIM OF PRIORITY

This application claims the priority from U.S. Provisional application Ser. No. 62/088,073 filed on Dec. 5, 2014, U.S. provisional application Ser. No. 62/063,031 filed on Oct. 13, 2014, and U.S. Provisional application Ser. No. 61/933,032 filed on Jan. 29, 2014, the contents of which are all incorporated by reference in their entirety.

The present invention relates to systems, compositions and methods to produce therapeutic bacteria phages capable of delivering nucleic acids to bacteria, modified phages and the use of the modified phages to deliver nucleic acids to bacteria. In this regard, the ability to deliver genetic information to cells and program the cells for the production of a therapeutic agent is a powerful tool amenable to several applications including human health, industrial production, agricultural production, biotechnology, and cosmetics.

The application of synthetic biology for humans and animals has dramatically improved the ability to cure diseases and ameliorate life style. In humans, synthetic biology applications are being applied to cellular and regenerative medicine with the intent to cure deadly diseases such as cancer, develop novel vaccines and regulate specific cellular functions and metabolism. In the agriculture field, conventional applications have initiated debates about the possibility of increasing crop production. Such applications may also help feed the world using synthetic biologic techniques.

Bacteria are an essential part of every living organism. All plants and animals, from protists to humans, live in close association with complex communities of microbial organisms. For example, the commensal bacterial flora (called the microbiome) composes about 90% of the total cells in the human body. Bacteria are present in the gut, mucosal tissues, and skin, as well as other environments in the body. Alterations of the commensal micro-organisms have been associated with several diseases, such as diabetes, irritable bowel syndrome, obesity, and cancer. In ruminants, complex microbiomes are essential to convert plant cell wall biomass into proteins and fatty acids, and companion animals display a highly complex microbial gastrointestinal ecosystem which influences disease states. Similarly, plants exhibit a broad range of relationships with symbiotic microorganisms that result in nutrient exchanges.

Over the past decade there has been considerable research directed towards understanding the relationship between the human body and the vast number of microbes that cohabitate it (i.e., the human microbiome). Commensal microorganisms outnumber human cells 9 to 1 and have received increased attention due to their essential importance in numerous human biological processes such as food digestion, metabolic regulation, biological barrier integrity, neurofunctions and regulation of the immune system. Specific bacterial populations are associated with specific regions and tissues of the human body, such as skin, gastrointestinal and respiratory tract, reproductive system and oral mucosa, and form a semi-continuous layer in direct contact with human cells and tissues. As such, these populations may occupy prime real estate niches for therapeutic intervention.

Complex communities of microorganisms are also found in the soil and water serving an essential role in the environment, decomposing dead materials, helping in cycling of minerals like carbon and sulfur, and enriching the soil with nitrogen, which is critical for plant growth.

As noted above, there are diverse and complex communities of bacteria found within specific environmental niches. The human intestine, for example, harbors an enormously complex, diverse, and vast microbial community, referred to as the gut microbiota (or microbiome). The human gut microbiota is estimated to consist of $10^{14}$ bacteria and archaea. In its entirety, the gut microbiota is estimated to contain 150-fold more genes than human host genomes. Apart from contributing substantial beneficial functions to the host, this unique and independent ecosystem has enormous potential for physiological and pathological interactions with the host, for example, as a target for the phage gene therapy embodiments described in the present invention. This also holds true for the human dermal and mucosal microbiota, as well as for the microbiota specific to animals, plants, and the environment (water and soil).

Phages in their most basic definition are viruses that infect bacteria. The use of phages for the treatment of bacterial infections (known as phage therapy) is known. For example, phages have been used in antibacterial therapy and biotechnology as antimicrobial targeting infectious agents for both medical and industrial purposes as well as for research in gene discovery and protein expression. In this regard, such phage therapy is the therapeutic use of bacteriophages to treat pathogenic bacterial infections. Such conventional phages have been used therapeutically to treat bacterial infections that do not respond to conventional antibiotic drugs. This treatment involves the infection of a pathogenic or targeted bacteria by the phage and destruction of the bacteria via the lytic cycle of the phage replication pathway, thus eliminating the bacteria. Conventional methods for creating and utilizing such bacteria phages for antimicrobial purposes have been developed and used primarily in Russia and Europe.

Phages have also been utilized for research of various prokaryotic and eukaryotic systems and many of the basic concepts of modern molecular biology are a result of studying the genetics of phages. Because phages can accommodate the insertion of large amounts of heterologous nucleic acids, the phage is an ideal vehicle for the cloning and expression of transgenic material. Indeed, several industrial and biotechnical applications of phage are known. Primary applications in biotechnology include the use of bacteria phage for nucleic acid or genetic "library" screening, the generation of single stranded DNA for sequencing (a utility which has become obsolete with advances in DNA sequencing technologies) and phage display. Such conventional technologies rely on the ability of the recombinant phage to replicate and form infectious particles that can be amplified either on their own or with the assistance of a helper phage.

For example, phage display is a laboratory technique for the study of protein-protein, protein-peptide, and protein-DNA interactions that uses bacteriophages to connect proteins with the genetic information that encodes them. In this technique, a gene encoding a protein of interest is inserted into a phage coat protein gene, causing the phage to "display" the protein on its outside while containing the gene for the protein on its inside, resulting in a connection between genotype and phenotype. These displaying phages can then be screened against other proteins, peptides or DNA sequences, in order to detect possible interaction between the displayed protein and those other molecules. In this way, large libraries of proteins can be screened and amplified in a process called in vitro selection. Such displaying phages are not designed to target particular bacteria but only to determine possible interaction with an array of proteins. For example, applications of phage display technology include determination of interaction partners of a protein (which would be used as the immobilised phage "bait" with a DNA library consisting of all coding sequences of a cell, tissue or organism) so that the function or the mechanism of the function of that protein may be determined.

It is also noted that the use of technologies to directly target and reprogram cells through gene replacement or by introducing a new gene or regulatory nucleic acid elements holds great therapeutic promises for treatment of human disease. Synthetic biology is becoming an indispensable tool for the generation and administration of innovative nucleic acid-based interventions including protein drugs, vaccines and gene therapies. Despite the broad therapeutic potential of nucleic acid therapy, there are major limitations to effective delivery and clinical utilization related to stability, pharmacokinetics, intracellular target accessibility, and specificity of target tissue. Many different approaches have been taken to overcome these limitations, such as different nucleic acid encapsulation strategies, mechanical and electrical techniques for introduction of nucleic acids into cells, and viral-based delivery systems. Despite some success in animal models, their use in humans has been impaired by short and long term efficacy and safety, immunogenicity, risk of insertional mutagenesis, nucleic acid size limitations, and cost. Therefore, there is a compelling and significant need for novel delivery vehicles that can efficiently, safely and affordably deliver therapeutic nucleic acids in vivo for the treatment of human disease.

However, nothing found in the prior art relates to the use of bacteriophages (phages) as a delivery vehicle for specific nucleic acids and genetic material that would be expressed by a target bacterium within the natural microbiota associated with an individual, animal or the environment. The use of phages as described in the various embodiments of the present invention is analogous to a mammalian virus-based gene therapy vector such as adenovirus and lentiviral vectors used for the targeted delivery and expression of genes in eukaryotic cells; however, the present invention relates to the expression of genes and gene products in prokaryotic cells.

Aspects of the present invention take advantage of the commensal relationship between the human host and the microbiome for the targeted delivery of nucleic acid therapies. In one embodiment, a novel platform technology is disclosed to effectively deliver nucleic acids to program bacteria for expression of therapeutic proteins and RNA molecules in vivo at sites of greatest significance for a particular disease. This approach has a higher local concentration of the therapeutic and reduces/minimizes systemic/off-target effects than conventional means. Bacteria associated with mucosal surfaces can also be exploited for the generation of novel vaccines that are more efficacious, safer and less expensive to produce than current vaccines. Furthermore, this embodiment can be used to deliver regulators of bacterial metabolism and gene expression to modulate critical interactions between the microbiome and the human host that are linked to disease states or microbial pathogenicity in humans.

Another embodiment of the present invention relates to biological particles based on a filamentous bacteriophage platform engineered to target specific bacteria within the microbiome of an organism for delivery of nucleic acid therapies and expression of therapeutic genes. The bacteriophage-derived nanoparticles (BNPs) target specific bacteria in vivo. The BNPs carry the nucleic acids encoding the therapeutic gene(s) of interest which, once delivered, will be expressed in the target bacteria. This embodiment differs from conventional approaches for nucleic acid delivery to eukaryotic cells and uses 'microbial gene therapy' as a method for nucleic acid delivery for the treatment of human disease. This embodiment also differs from conventional phage therapy which uses lytic phage for antibacterial purposes. The inventive delivery platform does not kill the bacteria; rather it takes advantage of live bacteria for expression of therapeutic nucleic acids in vivo, making the commensal organism a site-specific therapeutic "factory". This has the advantages of delivering therapeutic nucleic acids at the biological site of greatest significance for a specific therapy, thus increasing the local concentration of the wanted therapeutics and diminishing the systemic effects. For example, BNPs programmed with a luciferase reporter gene can be constructed and characterized in vitro and in vivo as a model for delivery of nucleic acids encoding peptide therapeutics.

Other aspects of the present invention allow for flexible, scalable, tunable delivery of genetic cargo to specific types of bacteria associated, for example, with the human gastrointestinal tract, respiratory tract, and skin. The types of bacteria include for example to *Pseudomonas* in the lung, *Staphylococcus* on the skin, and *Escherichia coli* in the gastrointestinal tract.

In another embodiment, an inventive delivery platform is tunable and capable of encoding single or multiple genes of various functions that may be placed under different regulatory control mechanisms and can be modified to deliver its payload to different commensal bacterial species. The delivery platform can be programmed for delivery of therapeutic DNA and RNA and has broad-based applications for expression of therapeutic proteins, vaccination strategies and modulation of bacterial biological pathways linked to human's health and disease.

Another aspect of the present invention uses the fact the BNPs are stable, amenable to many formulations, have no payload constraint in terms of nucleic acid sequence and no immunogenicity issues. The inherent high stability of phage particles, their ease of production and the modular nature of this delivery platform will allow the targeted delivery of nucleic acid therapeutics to strategic areas of the host.

Another aspect of the present invention relates to methods for the creation of therapeutic phage particles by modified bacteria containing helper phage sequences and by specific phagemids. Bacteria alone with or without the helper phage sequences cannot generate therapeutic phage particles. Likewise, phagemids encoding the therapeutic phage alone cannot generate the therapeutic phages. Specific therapeutic phage particles are generated only when bacteria are modified with both the modified helper phage sequences and the phagemids. In one aspect, embodiments of the present invention differ from that of phage display in that the therapeutic phage lacks specific phage genes such that therapeutic phage particles may only be formed in the context of the packaging cell line. Other embodiments of the present invention also differ from that of phage display technology in that the therapeutic gene sequence is inserted into the phagemid as an autologous gene cassette and not in frame with the pill protein coding sequence for display on the phage surface. In addition, in yet other embodiments, the therapeutic phage particles are used as delivery vehicles for the transduction of nucleic acid sequence into specific target bacteria in vivo (the host organism) or to bacteria in the environment.

Yet another embodiment of the present invention relates to a stable bacterial host strain that contains a modified helper phage genome, such as, but not restricted to, filamentous M13 helper phage of *Escherichia coli* (*E. coli*), integrated into a bacterial host genome, although application of the technology is not dependent on integration of the sequences into the host genome. A helper phage by definition is a phage that is able to supply packaging functions in trans to a filamentous phage that itself does not encode all the necessary genes for replication and packaging, but can be packaged into an infectious phage particle if introduced into a bacterial strain harboring the helper phage. The bacterial host strain is generated by transformation of a bacterial strain with a plasmid encoding modified helper phage genes. The bacterial strain may be any in which the modified helper phage and phagemid can function together to produce the specific therapeutic phage particle. For the purpose of illustration, *E. coli* is used as an example bacterial strain. In one embodiment, the modified helper phage encoded within the plasmid has the following attributes, 1) it is non-lytic; 2) encodes the phage enzymes and nucleic acid sequences necessary for replication and packaging of a heterologous phage supplied in trans by therapeutic phagemid sequences; 3) is devoid of a packaging signal, and 4) may have a non-antibiotic selectable marker.

Another embodiment of the present invention relates to the therapeutic phage genome contained in a phagemid. A phagemid by definition is a DNA plasmid that is capable of replication in bacteria as a plasmid and also encodes phage sequences, including a phage origin of replication and packaging signals that allow for replication and packaging of the encoded sequences into an infectious phage particle when present in a bacterial cell harboring a helper phage. In one embodiment, the phagemid genes encode a genetically engineered non-replicating, non-lytic phage with the following attributes: 1) the phagemid encodes the therapeutic gene sequence(s) under the regulatory control of a bacterial or phage promoter; 2) an origin of replication (ori) for replication in the host packaging strain; 3) the phage structural genes encoding elements necessary for recognition of a target bacterial strain (phage receptor binding protein (RBP)), attachment and entry into the targeted bacterial host; 4) signal sequences necessary for amplification and packaging by the helper phage functions; 5) may have a non-antibiotic selectable marker; multiple cloning sites flanking the therapeutic gene sequence(s), phage attachment and regulatory elements to allow for modular combinations of gene sequences; and/or 6) may contain sequence elements necessary for the integration of the phage into the target host genome.

The combination of the host packaging cell line and the therapeutic phagemid by transformation of the packaging cell line with the phagemid sequences results in the synthesis and packaging of the phagemid DNA into a bacteriophage particle that can act as a delivery vehicle for a specific therapeutic gene. The therapeutic phage generated by combination of the (modified) host packaging bacteria cell line and the phagemid present includes one or more key features such as 1—replication deficiency; 2—non-lytic; 3—carrying exogenous genetic material. This therapeutic bacteriophage particle may then be delivered to the site of therapy in which the target bacteria resides as specified by the RBP encoded in the therapeutic phagemid, and may be delivered according to any of the modes of therapeutic application as needed, described below.

Another embodiment of the present invention is directed to a method for the generation of a therapeutic phage including the steps of modifying a bacteria to contain a helper phage sequence, using a phagemid including a nucleic acid sequence and generating the therapeutic phage when the modified bacteria and the phagemid are together.

In general, the various aspects and embodiments of the present invention may be combined and coupled in any way possible within the scope of the invention. The subject matter that is regarded as the invention is particularly pointed out and distinctly claimed in the claims at the conclusion of the specification.

The foregoing and other features and advantages of the invention will be apparent from the following detailed description taken in conjunction with the accompanying drawings.

FIG. 1 shows a composition of a helper phage plasmid 1.

FIG. 2 shows an example of a packaging cell line (or a modified bacteria) 2.

FIG. 3 shows a composition of a phagemid 3.

Figure 4:
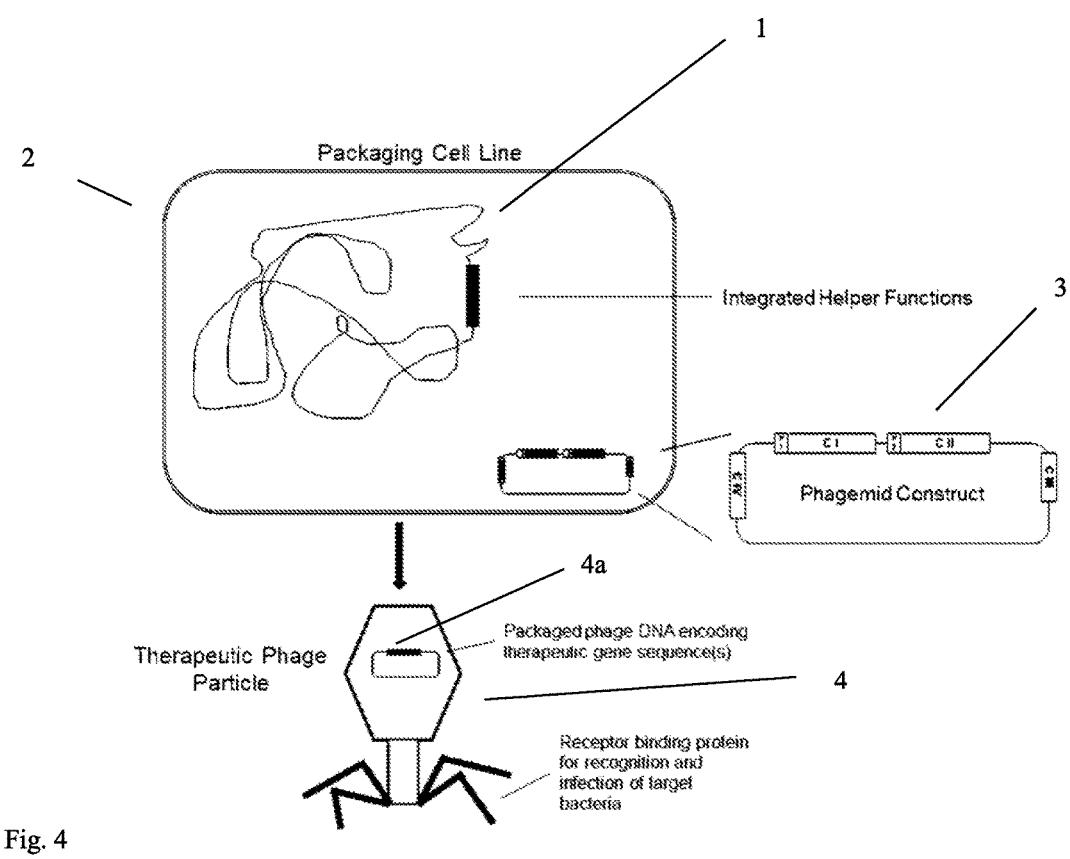
FIG. 4 shows a composition of a therapeutic phage particle 4.

As mentioned above, the modified bacteria 2 contains a (modified) helper phage sequences 1*a*. Such modified bacterium 2 can be generated several ways, e.g. utilizing molecular biology techniques and a bacterial transposon system. A specific phagemid 3 is constructed to encode phage infectivity sequence (pIII), phage packaging signal and the therapeutic gene (or genes) of interest. The expression of any sequences can be under the regulatory control of inducible promoters.

As shown in FIG. 1, the helper phage plasmid 1 includes sequences of a helper phage (Cassette I) containing genes that encode the packaging and replication functions for bacteriophage, but lacks a packaging signal and may lack a competent phage receptor binding protein (RBP), coding sequences that are determinants for packaging of a helper phage genome (packaging signal sequence) and specificity in infection by the phage (RBP). For example, the helper phage plasmid 1 may be sequences of the M13 filamentous helper phage, or other phage sequences or any combination thereof, necessary to replicate and package heterologous phage sequences in trans. Expression of the helper phage genes may be under the regulatory control of an inducible promoter, such that the phage proteins are only expressed upon activation by an added stimulus. In another embodiment, transcription of the helper phage genes may only be activated by protein(s) or peptide(s) encoded in the therapeutic phagemid 3 (FIG. 3). In this case, transformation of the host packaging strain with the therapeutic phagemid 3 would result in expression of the helper phage genes necessary to replicate and package the phagemid sequences resulting in coordinated production of the therapeutic phage particle 4 (FIG. 4).

The helper phage plasmid shown in FIG. 1 also encodes a non-antibiotic selectable marker (Cassette II) that allows for selection of the transformed host bacterial strain, which will harbor the helper phage elements. The selectable marker may encode a specific antitoxin necessary for replication of the transformed bacteria on growth medium containing the toxin, or may encode a metabolic function that allows the transformed bacteria to grow on medium deficient in an essential nutrient. In the case of the latter, the plasmid encoding the helper phage sequences would be transformed into an auxotrophic host strain for example, an *E. coli* strain that contains a deletion in the glyA gene. The glyA gene encodes serine hydroxymethyl transferase, an enzyme involved in the biosynthetic pathway for the amino acid glycine. This strain can grow only if glycine is added to the culture medium or if it transformed with a plasmid expressing a functional glyA gene.

As shown in FIG. 1, a third component (Cassette III) may also be present in the helper phage plasmid 1 that encodes sequences necessary for the stable integration of the plasmid into the bacterial host genome, although application of the technology is not dependent on integration of the sequences into the host genome. These sequences may be those of a bacterial transposon, or may be any other genetic element that facilitates stable integration into the host genome. Cassette IV in the helper phage plasmid 1 construct contains elements necessary for propagation and amplification of the plasmid sequences in host bacteria such as an E. coli origin of replication (Ori) and a selectable marker. In the case of Cassette IV, the selectable marker may confer antibiotic resistance. These sequences may be those of a common commercially available bacterial plasmid. Implied within the sequences are engineered and endogenous endonuclease restriction sites necessary for cloning and insertion of phage and associated gene modules, and transcriptional promoters and terminators necessary for regulation of bacterial and phage gene expression.

FIG. 2 shows an example of the packaging cell line 2 (i.e., a phage packaging strain or a bacterial strain) produced by transformation with the helper phage plasmid 1. The bacterial strain has the helper phage plasmid integrated into the bacterial chromosome. The bacterial strain may be any in which the modified helper phage sequence 1a and the specific phagemid 3 (FIG. 3) can function to produce the therapeutic phage particle 4 (FIG. 4). The bacterial strain is selected and the genotype maintained by culture on selective growth medium. The bacterial strain itself is incapable of producing infectious phage particles and the helper phage sequence 1a are incapable of transmission due to the lack of packaging signals in the helper phage sequence 1a. The stable integration of the helper phage sequences 1a into the host bacteria results in the insertion of Cassettes I and II into the host chromosome. Recombination necessary for insertion of Cassettes I and II would result in the loss of Cassette IV.

FIG. 3 shows an example of the phagemid 3 construct. The phagemid 3 includes phage sequences necessary for the synthesis and packaging of the encoded genome (Cassette I) in the presence of helper phage plasmid 1. In this regard, the encoded genome encodes a therapeutic function. The therapeutic function may be a known therapeutic value or an experimental therapeutic. In an example, a gene that encodes an enzyme that breaks down gluten (glutenase) for the treatment of gluten intolerance (e.g., celiac spruce disease) can be used in the phagemid 3. In this example, the therapeutic phage particle 4 (FIG. 4) would be one that targets a bacteria in the gut. When introduced into the gut, the therapeutic phage particle 4 containing the glutenase gene would infect the target bacteria in the gut, thereby causing the target bacteria to make and excrete the enzyme at the site in the body where it was needed. Modifications could be made to any of the therapeutic genes to regulate the level of expression or excretion from the host bacteria, or to help the therapeutic product to cross a biological barrier (such as the gut lumen) once it is expressed and excreted.

The applications are not limited to the gut, as there are commensal microbes associated with the oral cavity, nasal cavities, skin, etc that could be targeted with the therapeutic phage particles 4 of the present invention. The human scalp harbors a fascinating array of commensal bacteria (the microbiome) which form a continuous layer on the epidermis of the scalp. These commensal bacteria are also found in direct association with the hair follicle and in the subdermal tissues. Thus, the bacteria comprising the dermal microbiome occupy prime real estate for treatment of dermatological maladies and are an ideal target for in vivo gene therapy. As another example, the bacteria in the hair follicles can be targeted with a specific therapeutic phage particle 4 that encodes a protein that promotes hair growth.

The phage sequences in the phagemid 3 may also include genes that help maintain the stability of the phage in target bacteria. An example of maintenance genes include the Defense Against Restriction genes darA and darB of P1 phage to assist in the stability of the transduced DNA. The P1 phage genome is greatly protected from type I restriction and modification systems in target bacteria, even though P1 phage DNA is a good substrate for type I restriction enzymes in vitro. This protection is due to the presence of darA and darB gene products found in the phage head and injected into recipient cells along with the DNA. The therapeutic sequence(s) are encoded in Cassette II of the phagemid 3 construct and are expressed under the regulatory control of a bacterial or phage promoter (P2) that is functional in vivo in the target bacteria. The promoter may be constitutive in nature or may be regulated by environmental stimuli, such that the therapeutic gene(s) would be expressed at a steady rate, or only within the context of a specific environmental stimuli, respectively. The therapeutic sequence(s) may encode a single gene, multiple genes, chimeric proteins, DNA sequences or regulatory RNA such as small interfering RNA (sRNA), non-coding RNA or microRNAs (miRNA), or any precursor of such regulatory RNA molecules. Encoded proteins may include signal peptides to aid in the excretion of the gene product(s) and/or other specific sequences to aid in the delivery, stability and activity of the gene product, depending on the therapeutic application. Cassette III of the phagemid 3 encodes phage sequences including, but not limited to those which encode the receptor binding protein and determines the specificity and range of bacteria targeted for infection with the therapeutic phage particle 4. The phagemid 3 may also contain DNA elements that facilitate integration into the genome of the targeted bacteria.

For example, the g3p of the M13 bacteriophages consists of three globular domains: two N-terminal domains function in penetration and adsorption of the phage and the C-terminal domain anchors the g3p to the virion. This structure/function relationship of g3p has been used in the development and application of conventional phage display. However, by replacing the N-terminal domains of g3p in our platform therapeutic phagemid with phage sequences that specify infection of heterologous bacteria BNPs can be created that are capable of delivering nucleic acids to those bacteria at biologically relevant sites in vivo.

Once the helper phage plasmid 1 is inserted into the modified bacterium, specific therapeutic phage particles 4 are generated with the help of the phagemid 3. FIG. 4 shows the production of the therapeutic phage particle 4 by introduction of the phagemid 3 into the packaging cell line 2 (i.e., the bacterial strain). Transformation of the packaging cell line 2 with the phagemid 3 construct encoding the therapeutic gene sequence(s) and the receptor binding protein results in the production of the therapeutic phage particles 4. The therapeutic phage particles 4 may be delivered in vivo by a variety of routes (i.e. topical, oral, inhalation, vaginal, rectal, ocular, or any other perceived route of application) to infect the target bacteria, as determined by the recognition binding protein composing the therapeutic phage tail fibers. Infection of the target bacteria results in delivery of the therapeutic phage particles 4 and expression of the therapeutic gene sequence(s). The therapeutic phage particle 4 may also be applied to the environment (directly or indirectly) to an insect vector capable of transmission of a pathogen. This application, for example, includes the use of the therapeutic phage particle 4 containing one or more genes encoding a product that would disrupt the replication cycle of malaria or dengue virus within a mosquito host.

The therapeutic phage particle 4 may have several features such as being non-lytic and incapable of sustained independent replication. The lytic feature may be abrogated by mutations or deletion of the gene(s) responsible for it. Similarly, gene(s) that sustain phage replication in bacteria are silenced by deletion of the genetic material or by mutations. It is noted that the therapeutic phage particles 4 may be used in vivo. The therapeutic phage particles 4 may be specific for any species of bacteria or may infect a range of bacteria and the specificity will determine the site of delivery, i.e. phage specific for dermal microbes, microbes in hair follicles, microbes in the upper intestinal tract, in the lower intestinal tract, the duodenum, vaginal environment or any other specific site in humans or animals.

In one embodiment, the therapeutic phage particles 4 are used to infect specific bacteria within the microbiome of a host organism (human, animal, or plant) or within the environment (e.g., soil). In other embodiments, application of the therapeutic phage particle 4 is coupled with consumption of a target bacteria in the form of a probiotic preparation, a topical application, or other appropriate means of application.

For example, laboratory data supporting topical application has been demonstrated by a topical application of the therapeutic phage 4 and targeted expression of a report gene on mouse skin. This laboratory data was gathered by constructing a 2-plasmids system to generate therapeutic phage particles 4 that specifically contain the green fluorescent protein (GFP) sequence. Polymerase chain reaction (PCR) confirmed the generation of therapeutic phage particles 4 with the GFP sequence. The GFP carrying therapeutic phage particles 4 were used to deliver GFP into non-fluorescent bacteria on the mouse's skin.

More specifically, in the laboratory data, the bacteriophage nanoparticle (BNP) platform is composed of a therapeutic phagemid and a filamentous phage packaging plasmid. The therapeutic phagemid is a modular shuttle plasmid capable of replication in both the target bacterium and *E. coli*, used for production, and carries the therapeutic nucleic acids. In addition, the therapeutic plasgemid contains a filamentous phage origin of replication, a chimeric M13 phage g3p protein, for targeting of specific bacteria, and the packaging signal sequence, necessary for replication and incorporation of the phagemid ssDNA into the BNP. The packaging plasmid encodes sequences necessary for replication and assembly of the bacteriophage particle, but is devoid of the phage origin of replication, packaging signal, and g3p gene. The combination of the two plasmids results in the production of BNPs that contain only the phagemid DNA sequences and not the packaging plasmid. The laboratory data demonstrated the delivery of a reporter gene to *E. coli* in vitro and in vivo. The therapeutic phagemid was engineered based on the M13 bacteriophage to carry the GFP cDNA, ORI, g3p and packaging signal sequences. The packaging plasmid encodes sequences necessary for replication and assembly of the M13 bacteriophage. BNPs were generated by co-transfection of the two plasmids into competent DH5α cells and purified by PEG precipitation. Individual preparations of the GFP-programmed BNPs were prepared and used to transduce *E. coli*. The individual preparations were first assayed to assure selective packaging of the phagemid sequences into the BNP by PCR. *E. coli* K12 cells were then transduced with the six GFP-programmed BNPs and plated onto selective medium (kanamycin for the therapeutic phagemid selection) resulting in growth of bacteria transduced with BNPs only. When analyzed by flow cytometry, the transduced bacteria showed intense green fluorescent signal, demonstrating delivery and expression of the packaged genetic information. A skin-abrasion model on Balb/C mice was employed to test the ability of BNPs to deliver the nucleic acid cargo in vivo. *E. coli* bacteria were applied to the skin after mild abrasion and BNPs or vehicle alone (TBS) were topically added. *E. coli* transduced in vitro with the GFP-programmed BNPs were applied to the skin of mice as positive control. GFP expression was examined on areas of topical application by UV imaging and by flow cytometry in bacteria extracted from skin 24 hrs after application. Only mice that received BNPs showed fluorescent signal on skin and GFP expression in extracted bacteria by flow cytometry similarly to the positive control, confirming that the BNPs can successfully deliver the genetic cargo to *E. coli* in vivo.

The therapeutic phage particle 4 includes therapeutic gene(s) sequences 4a that may encode a single or multifunctional protein, peptide, nucleic acid such as miRNA, shRNA or sRNA, or any other envisioned molecule of therapeutic value. The therapeutic gene (or genes) 4a can encode for proteins, peptides, decoys, antibodies and any other therapeutically relevant molecules (called products). The encoded therapeutic product may be designed to be secreted from the infected bacterial host, or may be designed to be expressed on the surface of the infected host or may be designed to affect specific biological pathways in the targeted bacterial host. The therapeutic products can be secreted and have phenotypical effects on eukaryotic and/or prokaryotic target cells. The phenotypic changes are intended to be any modifications that lead to a biological effect or multiple effects. The therapeutic products can also affect internal biological pathways of the host bacteria cells or the eukaryotic cells. The therapeutic products can be exposed on the host cell membrane and non-secreted. The therapeutic products can be naïve or recombinant derived from molecular biology techniques of the nucleic acid material such as cloning, mutagenesis, recombination, or shuffling. The therapeutic products can also be non-therapeutic and produce phenotypic changes in prokaryotic and eukaryotic cells, such as skin tanning, teeth whitening or suppression of odor (sensory or creation). The therapeutic products can also affect the immune system by inducing an immune response or by creating immune tolerance.

As noted above, the therapeutic phage particles 4 can target a specific bacteria strain and/or the therapeutic phage particles 4 can have a broad spectrum of bacteria targets. The specificity is dictated by the capsid and recombinant pill, or tail fiber proteins that can be derived from one phage strain or can be a hybrid combination from two or more phage strains, or can be a hybrid of phage and any peptide or protein that facilitates attachment and entry of the particle to the target organism. The therapeutic phage particles 4 can be delivered using any appropriate pharmaceutical formulation, e.g., ointments, gels, patches, lotion, shampoo, beverage, or freeze dried phage, using one or more delivery routes, e.g., oral, topical, parenteral, mucosal, and may be formulated for time-release delivery. The pharmaceutical formulation can contain one strain of phages with proper bacteria specificity or two or more phage strains to target multiple bacteria strains.

The therapeutic phage particles 4 can be used for treatment of metabolic syndromes, oral hygiene, cosmetic products, vaccination, immunotolerance, protein replacements, agriculture, and industrial products, or any other envisioned appropriate therapeutic or cosmetic application.

For example, the therapeutic phage particles 4 can be applied to the environment (soil, or water) to eliminate a toxin or environmental contamination, such as in an industrial chemical spill or waste product. The therapeutic phage particles 4 can also be applied to waste water or industrial waste or byproduct to decontaminate or detoxify the waste. In this embodiment, the therapeutic phage particles 4 may be co-administered with the target bacteria. In yet other embodiments, the therapeutic phage particles 4 can applied to industrial or environmental material such as but not limited to agricultural or food production waste to produce or improve on the production a metabolic product.

Other aspects of the present invention are directed to delivery of vaccines. The majority of conventional vaccines are administered by intramuscular or subcutaneous injection, focused on eliciting a humoral response and resulting in effective protection against a wide range of diseases. However, this method of delivery is inadequate for vaccination against several important pathogens. It is now clear that both humoral and cellular responses play a pivotal role in protection against disease after vaccination. In some cases, nasal and lung vaccinations proved to be more effective than injection in inducing a protective immune response for both humoral and cellular. Protective mucosal immune responses are most effectively induced by mucosal immunization through oral, nasal, rectal or vaginal routes. However, there are challenges linked to the design of mucosal vaccines, such as dilution in mucosal secretions, entrapment in mucus gels, inactivation by proteases and nucleases, and exclusion by epithelial barriers. This means that relatively large doses of vaccine may be required for mucosal administration.

In this regard, the therapeutic phage particles 4 can be used to improve delivery of vaccines. The therapeutic phage particles 4 are used to target bacteria within the upper respiratory tract, lung or gut and deliver genes programmed to express appropriate antigens and/or immunomodulators, which results in T and/or B cell response. In this case, the target bacteria will express and excrete the antigenic protein and/or immunomodulator that will be recognized by neighboring immune cells, eliciting an immune response. This results in a stronger immune response due to the close relationship of commensal bacteria with lymphocytes. This approach has the advantage of enacting both the humoral and cellular arms of the immune system.

As an illustrative example, the following will detail the construction and characterization of bacteriophage nanoparticles specific for *E. coli* in vitro and in vivo. In this example synthetic biology and standard molecular techniques are used to produce BNPs encoding a luciferase reporter gene under the control of an *E. coli* σ-70 constitutive promoter. *E. coli* DH5α T1$^r$ cells transformed with reporter phagemid and M13 packaging plasmid can be cultured in 2XTY medium and particles will be PEG precipitated from culture medium.

As another illustrative example, the following will detail the construction and characterization of bacteriophage nanoparticles specific for *Pseudomonas aeruginosa* in vitro and in vivo. Two therapeutic shuttle phagemids encoding g3p minor coat protein chimeras consisting of the N-terminal sequence from *Pseudomonas* filamentous phage pf1 (ORF437) or pf3 (ORF483) and the C-terminal domain of M13 can be engineered for construction of phage particles specific *P. aeruginosa* strain PAK through interaction with the PAK pili, or PAO1 through interaction with the RP4 pili, respectively. The therapeutic phagemids also contain the Ori1600 and Rep protein necessary for replication and maintenance of the plasmid in *P. aeruginosa* along with elements necessary for production of the phage particles in *E. coli*. Expression of luciferase is placed under the control of the *E. coli* constitutive σ70 promoter, which along with the promoter driving kanamycin, is active in *pseudomonas*.

As another illustrative example, the following will detail the construction and characterization of bacteriophage nanoparticle specific for *Staphylococcus aureus* in vitro and in vivo, as a model Gram positive organism. The therapeutic phage particles 4 are modified for replication in *Staphylococcus* and chimeric g3p tuned for infection of *Staphylococcus aureus*. *Staphylococcus* is chosen as a model Gram positive organism for POC studies due to is wide distribution on the skin, in the nares and upper respiratory tract. The g3p sequences of the therapeutic phagemid are tuned to bind *Staphylococcus aureus* using phage display. Sequences for phage display screening are based on phage tail fiber regions of published *Staphylococcus* phages and *Staphylococcus* outer membrane binding domains of lysin molecules. Once identified, chimeric g3p sequences are subcloned into the therapeutic phage particles 4 containing the *Staphylococcus* replication elements and a *Staphylococcus* constitutive promoter driving the transcription of codon optimized luciferase. The therapeutic phage particles 4 can be amplified and BNPs are produced in SA80B *E. coli* cells (Lucigen) to circumvent the restriction properties of shuttle plasmids between *E. coli* and *Staphylococcus*.

The therapeutic phage particles 4 can be used to develop diagnostics kits for the detection of microbiome associated diseases. For example, such phages can detect changes in quality and number of specific bacteria associated with the microbiome alteration during diseases. Such phage diagnostic kits may use body fluids as well as tissues. The diagnostic function is achieved by using phages that carry genetic information encoding proteins suitable for imaging such as, for example, fluorescent proteins.

Similarly, the therapeutic phage particles 4 can be directly used in vivo for imaging purposes. One example the efficacy of pre and probiotics in favoring specific bacteria within the microbiome can be assessed. Such phages are administered in vivo via oral, topical, aerosol, parental and other appropriate ways. The expression on imaging protein from the bacteria targeted by such phages will allow in vivo imaging.

The therapeutic phage particles 4 can also be used for in vivo for delivery of nucleic acids encoding immunoregulatory proteins. In this regard, *P. aeruginosa* is a significant opportunistic pathogen. In cystic fibrosis (CF) patients, whose abnormal airway epithelia allow long-term bacterial colonization of the lungs. The combination of persistent infection, abnormal mucous, and local inflammation ultimately lead to pulmonary failure and death. CF patients are frequently treated with agents to suppress inflammation, such as systemic corticosteroids, however with significant adverse consequences of such therapy. Interleukin (IL)-10 is an important immunoregulatory cytokine whose expression is diminished in CF [47]. IL-10 limits and terminates inflammatory responses and regulates the differentiation and proliferation of several immune cells such as T cells, B cells, natural killer cells, antigen-presenting cells, mast cells, and granulocytes. In addition, IL-10 has been shown to mediate immunostimulatory properties that help to eliminate infectious and noninfectious particles with limited inflammation.

IL-10/IL-10 receptor system is now seen as a new therapeutic target and recombinant human IL-10 is currently being tested in clinical trials for many indications such rheumatoid arthritis, inflammatory bowel disease, psoriasis, organ transplantation, and chronic hepatitis C. Local delivery to the site of inflammation has advantages over systemic targeting of this pathway. Therefore, a method for in vivo delivery of nucleic acids for site-specific expression of IL-10 would have broad range therapeutic benefit. The therapeutic phage particles 4 (e.g., pf3 pseudomonas phagemid) can be used to express secreted forms of IL-10 in P. aeruginosa PAO1.

The therapeutic phage particles 4 can also be used for in vivo for delivery of RNA-based nucleic acid therapies. BNPs can be developed for the delivery and expression of genes encoding siRNA to regulate bacterial gene expression in *Pseudomonas* and to program *E. coli* for the delivery of shRNA to eukaryotic cells for trans-kingdom RNAi. The use of regulatory RNA has received great attention as a as a novel treatment of many diseases failing conventional small molecule therapy. The use of therapeutic ribozymes, apatamers, and small interfering RNA (siRNA) in post-transcriptional gene silencing (PTGS) has demonstrated the broad potential and utility of RNA-based nucleic acid therapeutics in recent clinical trials. However, effective delivery of RNA is hampered by significant biological and biophysical barriers inherent in the RNA molecule, such as its instability, potential immunogenicity, and the need for a synthetic or biological-based delivery vehicle. However, the therapeutic phage particles 4 can be tuned to effectively deliver RNA-based nucleic acid therapies to the microbiome for regulation of bacterial gene expression and the delivery of shRNA to mammalian cells.

In this regard, Small RNAs (sRNA) are known be present in and play a regulatory role in signal transduction and metabolism in bacteria. Interactions between prokaryotic sRNA and its target mRNA is sequence specific, mediated by bacterial chaperones, and usually results in the suppression of targeted gene translation. Cross-talk between the commensal organisms themselves and host cells plays a role in maintaining a healthy homeostasis. Disruption of the healthy state of the microbiome (dysbiosis) has been associated with a multitude of disease states and may be a result of an alteration of microbial gene expression and metabolism in the native microbiome. Bacteriophage nanoparticle technology can be tuned to effectively deliver RNA-based nucleic acid therapies to the microbiome for regulation of bacterial gene expression.

In another example, the therapeutic phage particles 4 can also be used for the delivery of nucleic acids to *Porphyromonas gingivalis* in the oral cavity. As background, the treatment of oral and periodontal diseases and associated anomalies accounts for a significant proportion of the healthcare burden, with the manifestations of these conditions being functionally and psychologically debilitating. Periodontitis is chronic inflammatory disease with high morbidity in the adult population. It typically leads to the destruction of the tooth-supporting structures such as the gingiva and the underlying alveolar bone, and it has been linked to adverse systemic health, such as atherosclerosis, diabetes, rheumatoid arthritis, and adverse pregnancy outcomes. One of the hallmarks of periodontitis is the massive accumulation of neutrophils, thus linking the disease to an imbalance of the immune system. *Porphyromonas gingivalis*, a component of the oral microbiome, has long been associated with human periodontitis and recent studies suggest that *P. gingivalis* is a keystone organism leading to microbial dysbiosis and a pro-inflammatory response. Overall, *P. gingivalis* can impair host defenses in ways that alter the growth and development of the entire microbial community, thereby triggering a destructive change in the normally homeostatic relation with the host. Crosstalk between *P. gingivalis* with cells of the immune system, such as dendritic cells, can lead to the recruitment of pro-inflammatory T cells. Moreover, *P. gingivalis* inhibits production of Th1-recruiting chemokines as well as cell production of interferon IFNγ. The fact that the irreversible tissue damage is ultimately inflicted by the inflammatory host responses suggest that traditional treatments for periodontitis, such as scaling, root planning, use of antibiotics and surgical options, may not be sufficient to cure the disease, but strategies that target host signaling pathways needs to be considered. Pharmacologic anti-inflammation interventions were efficacious in preventing and slowing the progression of periodontal diseases in animals and man. However, the side-effect profile of such therapies precluded the use of non-steroidal anti-inflammatory drugs. In addition to treating the disease, a challenge faced by periodontal therapy is the regeneration of periodontal tissues lost as a consequence of disease. Growth factors are critical to the development, maturation, maintenance and repair of oral tissues as they establish an extra-cellular environment that is conducive to cell and tissue growth.

In this regard, by replacing the N-terminal domains of g3p with sequences that specify absorption to and infection of *P. gingivalis* will create bacteriophage particles capable of delivering nucleic acids to bacteria in vivo. A two-step process can be used to identify g3p sequences that promote specific absorption and entry of BNPs into *P. gingivalis* expressing FimA fimbriae. *P. gingivalis* fimbriae are analogous to pili on the surface of *E. coli. P. gingivalis* fimbriae are adhesive filamentous appendages and a major virulence factor for *P. gingivalis* participating in nearly all interactions between the bacterium and the host, as well as with other bacteria. In humans, fimbriated *P. gingivalis* is readily detected in periodontal pockets and is more frequently found in sites with severe periodontal attachment loss than non-fimbriated strains. As such, *P. gingivalis* strains that express FimA are candidates for effective microbial gene therapy in the control and treatment of periodontal disease.

In step 1, phage display using *E. coli* modified to express *P. gingivalis* FimA is used to select and amplify g3p sequences for absorption of bacteriophage particles to *P. gingivalis*. Type I FimA are amplified by PCR from *P. gingivalis* ATCC 33277 and subcloned into an *E. coli* pET expression vector encoding the transmembrane signal from *Pseudomonas aeruginosa* EstA (NCBI Accession number AF005091) as an anchoring motif for display of recombinant proteins on the surface of *E. coli. E. coli* BL21(DE3) cells (F-, ompT) are transformed with the Type I FimA expression plasmid to create a stable cell line for the inducible expression of surface expressed *P. gingivalis* Type I FimA. Phage display vector fADL-1 are modified to encode a PIII protein with a random mutagenized DII in the g3p N2 domain (fADL-1-mN2). Gene blocks containing mutated DII-N2 sequences are synthesized and placed into the fADL-1 vector. The fADL-1-mN2 plasmids and a pool of phage expressing the mutated PIII are propagated in electrocompetent F1-*E. coli* TG1 DUOs. The phage particles are used to infect the Type I FimA expressing cells, and phage are amplified in and purified from the infected cells. ssDNA is isolated from purified phage and the sequence of g3p N2 determined.

In step 2, the identified g3p N2 sequences conferring absorption to *P. gingivalis* Type I FimA are subcloned into a phagemid shuttle vector capable of replication in both *E. coli* (for amplification of plasmid DNA and production of BNPs) and *P. gingivalis*. The shuttle phagemid, in addition to sequences for propagation on *E. coli*, contain the minimum origin of replication for *P. gingivalis* and the erythromycin resistance cassette from plasmid pTO-1, a luciferase reporter gene under the transcriptional control of a *P. gingivalis* promoter, and the chimeric g3p containing a randomized mutations in the N-terminal region of the N1 domain of g3p (see FIG. 5). *E. coli* TG1 DUO cells are co-transformed with the shuttle phagemid and M13 packaging vector (containing a chloramphenicol [cat] resistance cassette) and transformed TG1 DUOs selected and propagated in 2XTY plus kanamycin and chloramphenicol. Phage particles are isolated and concentrated from the culture medium by PEG precipitation. Infected *P. gingivalis* are plated onto TSA blood agar plus containing erythromycin and plasmids purified from single colony isolates will sequenced for determination of g3p sequences conferring infection of *P. gingivalis* ATCC 33277. The identified g3p sequences are subcloned into the shuttle phagemid encoding a codon optimized nanoluciferase (nLuc) reporter gene [REF] and BNPs programmed with a luciferase reporter gene are constructed in *E. coli* and characterized for delivery of nucleic acids encoding peptide therapeutics to *P. gingivalis* in vitro and in vivo.

The BNPs generally are specific for Type I FimA *P. gingivalis* strains due to the antigenic differences of the FimA proteins. However, the range of the BNPs can be expanded, or tuned to specific FimA proteins, using the *E. coli* FimA expression plasmid to encode alternate FimA proteins.

By using such BNPs, nucleic acid therapies to *P. gingivalis* can be delivered for the effective local expression of immunoregulatory proteins and a reduction in the inflammatory responses associated with periodontal disease. For example, the BNPs can be for delivery of IL-10 to *P. gingivalis*. The therapeutic phage particles 4 encode a codon optimized IL-10 containing signal sequences for POR secretion system of *P. gingivalis*. IL-10 is an immunoregulatory cytokine that limits and terminates inflammatory responses, including the expression of IL-1β and TNFα, and regulates the differentiation and proliferation of several immune cells to mediate immunostimulatory properties that help to eliminate infectious and noninfectious particles. The POR secretion system in *P. gingivalis* uses a channel complex to secrete substances containing C-terminal peptide signals in from the cytoplasm across the inner and outer membranes to the outer bacterial surface and into the extracellular space. Phagemids are modified to express codon optimized rIL-10 or with a C-terminal POR secretion signal (CTD). Phagemids expression nLuc with the CTD POR secretion signal are engineered for use as a control. nLuc is an ATP-independent bioluminescent enzyme.

Local delivery to the site of inflammation has advantages over systemic targeting of this pathway and has therapeutic benefit beyond that of *P. gingivalis* infection and periodontal disease including other oral indications, inflammatory bowel disease and wound healing. The use of the POR secretory pathway allows selective expression of the protein into the surrounding extracellular space. Many gram negative bacteria express a Type 1 secretory system which uses a 3-component channel complex to secrete substances containing C-terminal peptide signals in one step from the cytoplasm across both the inner and outer membrane and into the extracellular space. While *P. gingivalis* does not possess a T1 SS, the embodiments described above have applications beyond the delivery of IL-10 to *P. gingivalis.*

It is also noted that the range of BNPs to target FimA *P. gingivalis* genotypes may be expanded. The FimA expression plasmid can encode sequences for FimA Types II-V and used for selection of BNP particles to transduce additional *P. gingivalis* strains. The expression plasmid can express a FimA consensus sequence and peptides encoding homologous regions between the FimA proteins to generate a ubiquitous BNPs for transduction of *P. gingivalis*. In addition, nucleic acid sequences encoding sRNA can be expressed. *P. gingivalis* harbors an arsenal of virulence factors, which along with its many interactions with the host immune system strongly support its potency as a pathogen. *P. gingivalis* also expresses a wide variety of sRNA in response to different environmental stimuli. The BNPs for the expression of sRNA can be used to regulate virulence factors.

The foregoing detailed description has set forth a few of the many forms that the invention can take. The above examples are merely illustrative of several possible embodiments of various aspects of the present invention, wherein equivalent alterations and/or modifications will occur to others skilled in the art upon reading and understanding of the present invention and the annexed drawings. In particular, regard to the various functions performed by the above described components (devices, systems, and the like), the terms (including a reference to a "means") used to describe such components are intended to correspond, unless otherwise indicated to any component, such as hardware or combinations thereof, which performs the specified function of the described component (i.e., that is functionally equivalent), even though not structurally equivalent to the disclosed structure which performs the function in the illustrated implementations of the disclosure.

Although a particular feature of the present invention may have been illustrated and/or described with respect to only one of several implementations, such feature may be combined with one or more other features of the other implementations as may be desired and advantageous for any given or particular application. Furthermore, references to singular components or items are intended, unless otherwise specified, to encompass two or more such components or items. Also, to the extent that the terms "including", "includes", "having", "has", "with", or variants thereof are used in the detailed description and/or in the claims, such terms are intended to be inclusive in a manner similar to the term "comprising".

The present invention has been described with reference to the preferred embodiments. However, modifications and alterations will occur to others upon reading and understanding the preceding detailed description. It is intended that the present invention be construed as including all such modifications and alterations. It is only the claims, including all equivalents that are intended to define the scope of the present invention.

The invention claimed is:

1. A method for delivering a nucleic acid sequence comprising the steps of:

administering to a subject a bacteriophage-derived particle including at least one nucleic acid sequence and a bacterial origin of replication and a receptor binding protein where the particle is devoid of one or more functional phage replication genes rendering it incapable of independent production of phage progeny;

wherein the receptor binding protein attaches the particle to a target bacteria in a microbiome; and wherein the nucleic acid sequence is expressed in the target bacteria where the expression of the nucleic acid sequence and the expressed nucleic acid sequence are non-lethal to the target bacteria and the expressed nucleic acid sequence produces a therapeutic effect to the subject.

2. The method according to claim 1, wherein the nucleic acid sequence is DNA and/or RNA.

3. The method according to claim 1, wherein the nucleic acid sequence encodes regulatory sequences for in vivo expression and targeting of the therapeutic effect.

4. The method according to claim 2, wherein the RNA is a trans-kingdom RNAi for expression in a microbiome and delivery, in vivo, to another cell.

5. The method according to claim 1, wherein the microbiome is associated with a living organism.

6. The method according to claim 1, wherein the nucleic acid sequence also encodes at least one element capable of facilitating stable integration of a therapeutic element, which may include regulatory sequences, into a genome of the target bacteria.

7. The method according to claim 5, wherein the attaching occurs in or on a gastrointestinal tract, respiratory tract, oral cavity, nasal cavity or surface of the living organism.

8. The method according to claim 1, wherein the nucleic acid sequence encodes an enzyme that breaks down gluten for treatment of gluten intolerance.

9. The method according to claim 1, further comprising the step of controlling the expression of the nucleic acid sequence under regulatory control of a bacterial or phage promoter that is functional in the target bacteria, wherein the promoter is constitutive in nature or regulated by environmental stimuli.

10. The method according to claim 5, wherein the administration is topical, oral, inhalation, vaginal, rectal, ocular, spread, sprayed, distributed, injected, or dropped application route.

11. The method according to claim 1, wherein the nucleic acid sequence expressed in the target bacteria elicits an immune response.

12. The method according to claim 1, wherein the expression of the nucleic acid sequence is for the treatment of dermatological maladies, cosmetic application, and/or hair loss.

13. The method according to claim 1, wherein the expression product of the nucleic acid sequence is an antigenic protein and/or immunomodulator.

* * * * *